(12) United States Patent
Cervantes

(10) Patent No.: US 8,794,437 B2
(45) Date of Patent: *Aug. 5, 2014

(54) PACKAGED SYSTEM INCLUDING A PROTECTIVE HOUSING FOR A TREATMENT DEVICE CARRIED ON A CATHETER

(75) Inventor: Marvin Cervantes, Edmonton (CA)

(73) Assignee: Medtronic Vascular, Inc., Santa Rosa, CA (US)

( * ) Notice: Subject to any disclaimer, the term of this patent is extended or adjusted under 35 U.S.C. 154(b) by 1699 days.

This patent is subject to a terminal disclaimer.

(21) Appl. No.: 11/782,357

(22) Filed: Jul. 24, 2007

(65) Prior Publication Data

US 2008/0011640 A1 Jan. 17, 2008

Related U.S. Application Data

(63) Continuation of application No. 11/056,933, filed on Feb. 11, 2005, now Pat. No. 7,261,205.

(60) Provisional application No. 60/543,960, filed on Feb. 12, 2004.

(51) Int. Cl.
*A61B 17/06* (2006.01)
*B65D 81/20* (2006.01)

(52) U.S. Cl.
USPC .......................... 206/364; 206/438; 206/363

(58) Field of Classification Search
USPC ........ 206/210, 571, 363–367, 438, 439, 63.3, 206/524.8
See application file for complete search history.

(56) References Cited

U.S. PATENT DOCUMENTS

| | | | |
|---|---|---|---|
| 4,154,342 A * | 5/1979 | Wallace | 206/439 |
| 4,928,830 A | 5/1990 | Brewer | |
| 5,022,527 A | 6/1991 | Braeutigam | |
| 5,031,768 A * | 7/1991 | Fischer | 206/370 |
| 5,133,454 A | 7/1992 | Hammer | |
| 5,601,532 A * | 2/1997 | Gaba | 604/110 |
| 5,690,117 A * | 11/1997 | Gilbert | 600/463 |
| 6,595,362 B2 | 7/2003 | Penney et al. | |
| 6,871,740 B1 * | 3/2005 | Cao | 206/364 |
| 6,896,141 B2 | 5/2005 | McMichael et al. | |
| 7,152,732 B2 * | 12/2006 | Clark | 206/308.1 |
| 7,261,205 B2 * | 8/2007 | Cervantes | 206/364 |
| 7,353,946 B2 * | 4/2008 | Cervantes | 206/428 |
| 2002/0062108 A1 | 5/2002 | Courteix | |
| 2002/0130059 A1 * | 9/2002 | Armijo | 206/438 |
| 2004/0215143 A1 * | 10/2004 | Brady et al. | 604/122 |

* cited by examiner

*Primary Examiner* — Steven A. Reynolds

(57) ABSTRACT

The present invention is a packaged system that includes a housing to protect a treatment device mounted on a distal portion of a catheter. The housing holds the device suspended such that there is little or no contact between the housing and the device, protecting the device from physical damage and also from exchange of chemical components between the device and the packaging materials, which can occur when a device remains in contact with packaging materials over an extended period of time. A port in the housing allows a controlled environment, for example a vacuum, to be maintained within the housing. A hollow stylet inserted into the distal end of the catheter before the catheter is placed in the housing precludes compression of the catheter and provides an injection port through which the catheter may be flushed with a fluid prior to use, eliminating the need for a separate flushing cannula.

24 Claims, 4 Drawing Sheets

US 8,794,437 B2

PACKAGED SYSTEM INCLUDING A PROTECTIVE HOUSING FOR A TREATMENT DEVICE CARRIED ON A CATHETER

RELATED APPLICATIONS

This application is a continuation application of and claims the benefit of U.S. patent application Ser. No. 11/056,933 filed Feb. 11, 2005, which claims the benefit of U.S. Provisional Application No. 60/543,960 filed Feb. 12, 2004, the entirety of which are incorporated herein by reference.

TECHNICAL FIELD

This invention relates generally to packaging systems for medical catheters. More specifically, the invention relates to a packaged system for treating a vascular condition that protects a treatment device carried on a catheter.

BACKGROUND OF THE INVENTION

Heart disease, specifically coronary artery disease, is a major cause of death, disability, and healthcare expense in the United States and other industrialized countries. In atherosclerosis, one form of heart disease, deposits of hard plaques (atheromas) may be formed within the intima of a vessel and inner media of arteries. This atherosclerotic disease process leads to a critical stenosis of the affected coronary artery and produces anginal syndromes, known commonly as chest pain. The progression of the stenosis reduces blood flow, triggering the formation of a blood clot (thrombus). The clot may further reduce or entirely prevent the flow of oxygen-rich blood to heart muscles, causing a heart attack. Alternatively, the clot may break off and lodge in the vessel of another organ, such as the brain, resulting in a thrombotic stroke.

One method for treating atherosclerosis and other forms of coronary narrowing is percutaneous transluminal coronary angioplasty (PTCA). During PTCA, commonly a balloon catheter device is inflated within the stenotic vessel. Upon inflation, the pressurized balloon exerts a compressive force on the lesion, thereby increasing the inner diameter of the affected vessel.

Soon after the procedure, however, a significant proportion of treated vessels restenose. To prevent restenosis, a stent may be implanted within the vessel. The stent acts as a scaffold to support the lumen in an open position and maintain lumen size. For insertion, the stent is affixed in a compressed configuration along the delivery catheter, for example crimped onto a balloon that is folded or otherwise wrapped about a guidewire. After the stent is properly positioned within the vessel, it is expanded, causing the length of the stent to contract and the diameter to expand.

Because stent insertion can cause undesirable reactions such as inflammation, infection, thrombosis, or proliferation of cell growth that occludes the passageway, stents are sometimes coated with therapeutic agents to assist in preventing these conditions. The coatings are bioengineered to release precise doses of the therapeutic agent. However, if the coating remains in direct contact with another material for an extended period of time, for example during shipping and storage, components of the therapeutic agent may migrate into the other material, resulting in delivery of a lower dose of the therapeutic agent than intended. Alternatively, components of a packaging material may migrate into the therapeutic coating, again leading to impaired performance of the therapeutic agent. Contact with packaging material may damage a coating even when it does not contain a therapeutic agent. Coated stents may also be damaged by exposure to ultraviolet radiation, and both coated stents and stents that have been surface treated may be affected by moisture in the air surrounding the stent.

Therefore, it would be desirable to have a packaged catheter system with improved protection for a treatment device such as a coated stent that overcomes the aforementioned and other disadvantages.

SUMMARY OF THE INVENTION

The present invention is a packaged system for treating a vascular condition. One aspect of the system comprises a treatment device, a catheter bearing the treatment device on a distal portion of the catheter, and a housing designed to receive the catheter portion bearing the treatment device. The housing, which includes a first portion rotatably attached to a second portion, suspends the treatment device in a protective well.

In another aspect, the packaged system for treating a vascular condition comprises a treatment device, a catheter bearing the treatment device on a distal portion of the catheter, and a housing including first and second portions. The treatment device is suspended between the two housing portions in a protective well. The protective well is subjected to a controlled environment via an environmental control port included in the first or the second housing portion.

In still another aspect, the packaged system for treating a vascular condition comprises a treatment device, a catheter bearing the treatment device on a distal portion of the catheter, a housing to receive the treatment device and suspend the device in a protective well, and a hollow stylet. The stylet is received within a distal end of the catheter and provides an injection port to allow the catheter to be flushed with a fluid prior to use.

The aforementioned and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof. The drawings are not to scale.

DETAILED DESCRIPTION OF THE PRESENTLY PREFERRED EMBODIMENTS

The present invention is a packaged system for treating a vascular condition. The described embodiments are designed to protect a coated stent. However, it is anticipated that the system may protect an uncoated stent, an angioplasty balloon, a biologic or drug delivery system, an electronic device, or any other treatment device carried on a catheter.

Figure 1A:
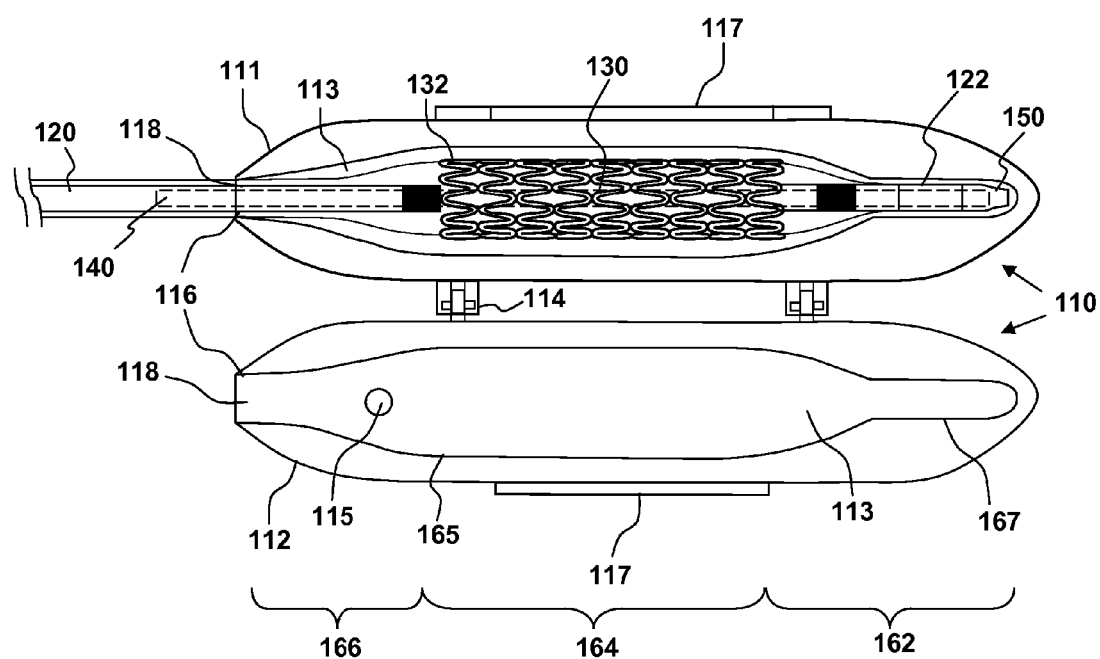
FIG. 1A is an illustration of one embodiment of a packaged system for treating a vascular condition, in accordance with the present invention.
Figure 1B:
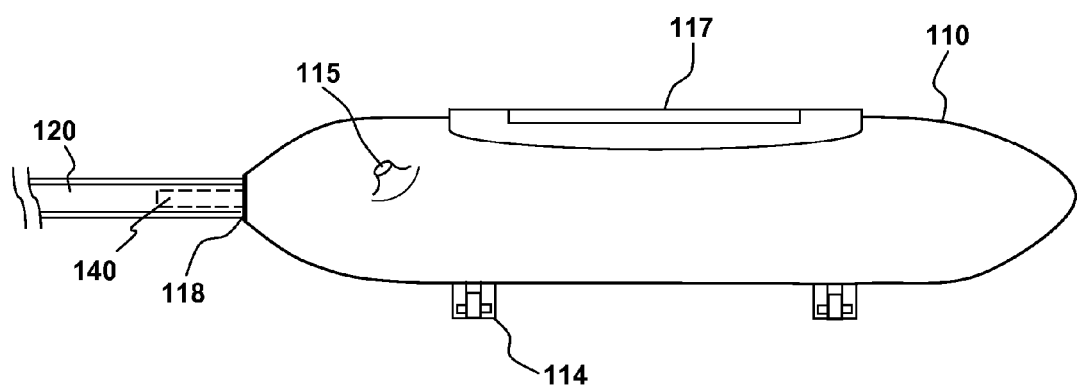
FIG. 1B shows the system of FIG. 1A as it appears when the housing is closed.

One embodiment in accordance with the present invention is illustrated in FIGS. 1A and 1B. The system comprises a housing 110, a catheter 120 bearing a stent 130, and a stylet 140. Housing 110 includes a first housing portion 111 rotatably attached to a second housing portion 112. As illustrated, housing 110 may further include hinges 114, an environmental control port 115, a sealing member 116, and a latching mechanism 117.

A protective well 113 is formed within the housing 110. Protective well 113 includes central portion 164, distal portion 162 and proximal portion 166. Distal portion 162 tapers distally from central portion 164. Proximal portion 166 tapers proximally from central portion 164.

Distal portion 162 of protective well 113 receives the distal tip 122 of catheter 120 that bears stent 130, and suspends stent 130 in central portion 164 of protective well 113. In one embodiment, distal tip 122 is held within distal portion 162 by a friction fit. In one embodiment, distal portion 162 includes an elongate receiving portion 167 for receiving and holding distal tip 122. In one embodiment, elongate receiving portion 167 extends distally from distal portion 162. In one embodiment, the diameter of receiving portion 167 is substantially the same as the outer diameter of distal tip 122 such that the distal tip 122 is held within receiving portion 167 with an interference fit. In one embodiment, receiving portion 167 is sized to receive cap 150 disposed on distal tip 122.

First housing portion 111 is rotatably attached to second housing portion 112 by hinges 114. Housing 110 can be rotated open, as shown in FIG. 1A, to facilitate placing a distal portion of catheter 120 within the housing. When housing 110 is closed, as shown in FIG. 1B, stent 130, which is carried on catheter 120, is suspended within central portion 164 of protective well 113, ensuring there is no contact between the outer surface 132 of stent 130 and the inner surface 165 of the central portion 164 of housing 110. In one embodiment, when housing 110 is in the closed position, the central portion 164 of protective well 113 has a well diameter defined by the inner surface 165 of housing 110 that is greater than the outer diameter of stent 130 as it is crimped or otherwise placed on catheter 120.

A proximal portion of catheter 120 extends out from housing 110 through opening 118. In the present embodiment, stylet 140 is received within a distal portion of catheter 120, and a cap 150 is removably attached to the distal end of stylet 140.

Housing 110 includes an environmental control port 115 through which the internal environment of the housing may be controlled. Ambient air may contain moisture and contaminants that could damage a coated or treated stent. Port 115 may be used to withdraw the ambient air from within housing 110, resulting in a vacuum within the housing. The vacuum may also be released through port 115. Alternatively, port 115 may be used to replace the ambient air within the housing with an inert gas such as nitrogen.

A sealing member 116, for example a gasket, aids in maintaining a controlled environment within housing 110. When housing portions 111 and 112 are rotated closed, sealing member 116 seals the edges of the two portions one to the other. The same or a separate sealing member encircles catheter 120 at opening 118, sealing housing 110 at the point where the proximal portion of catheter 120 extends out from the housing. Where one or both of the material and the structure of housing 110 permits the edges of the housing to be self-sealing, a separate sealing member may be unnecessary or may be needed only within opening 118.

Latching mechanism 117 holds the two portions of housing 110 in a closed position. The latching mechanism may be attached to housing 110 or may be formed integral with housing portions 111 and 112. A friction latch is illustrated; however, one skilled in the art will recognize that any appropriate latching mechanism known in the art may be used. For example, a band placed around the closed housing may be adequate. The latching mechanism may be eliminated, if desired, when a vacuum will be pulled within housing 110, the vacuum serving to hold the two portions of housing 110 in a closed position.

Stylet 140 is inserted into a distal end of catheter 120, typically within an inner member of the catheter, before the catheter is placed into housing 110. The stylet extends to at least the proximal edge of housing 110 to preclude catheter 120 being compressed by the edges of opening 118 when the catheter is closed in housing 110. Stylet 140 also serves as a sub-support for catheter 120 to prevent radial compression of the catheter lumen when a vacuum is pulled within housing 110 or when a gas is delivered into the housing.

A solid wire stylet is adequate to prevent compression of catheter 120. However, a hollow stylet offers the additional benefit of providing a port through which a fluid may be injected into catheter 120 using a syringe and needle. A saline solution is commonly flushed through a catheter immediately prior to use to confirm patency of the catheter and to increase lubricity of the inner lumen of the catheter, for example to aid in passing the catheter over a guidewire. By serving as an injection port into which the needle is placed, the hollow stylet protects the catheter's tip from being damaged by the needle. Because the hollow stylet is inserted into the catheter prior to shipment, the end user need not employ a separate flushing cannula, often provided by catheter manufacturers to be inserted into the tip of a catheter, saving the end user time when preparing the catheter for use.

As shown in FIG. 1A, cap 150 may be placed on the distal end of a hollow stylet 140 before catheter 120 is placed into housing 110. The cap seals the stylet and allows a controlled environment to be maintained within the housing. A cap is not required if the environment within the housing will not be controlled.

Housing 110 may comprise one or more suitable materials that can be conventionally formed and processed. Materials such as aluminum, stainless steel, polypropylene, polyethylene, polytetrafluoroethylene (PTFE), or a nylon/polyethylene blend may be used to provide additional protection for a coated stent by minimizing exchange of chemical components between the housing and the stent should the stent inadvertently come into contact with the housing during shipment and storage.

Housing 110 may be formed using one or more methods such as blow molding or injection molding. As just one example, housing 110 may be injection molded using PTFE, and an aluminum coating may be applied to one or both of the interior and exterior surfaces of the housing. PTFE and aluminum do not react with most stent coatings, and aluminum offers the additional benefit of protecting the stent from ultraviolet rays, which can damage some coatings.

One skilled in the art will recognize that various modifications may be made to the above-described embodiment. For example, housing 110 may be fabricated without an environmental control port if the treatment device contained within the housing is not negatively affected by ambient air.

In another modification, housing 110 may include a second opening at the distal end of the housing to permit the distal end of hollow stylet 140 and cap 150 to extend through the distal end of housing 110. This would allow the catheter to be flushed with the housing in place, further protecting a coated stent from contact with the fluid used to flush the catheter.

Figure 2A:
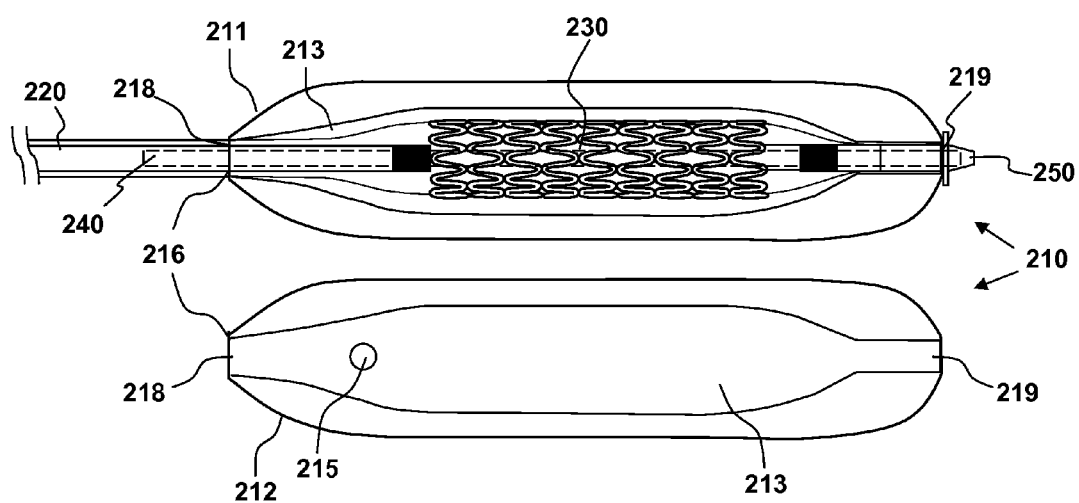
FIG. 2A is an illustration of another embodiment of a packaged system for treating a vascular condition, in accordance with the present invention.
Figure 2B:
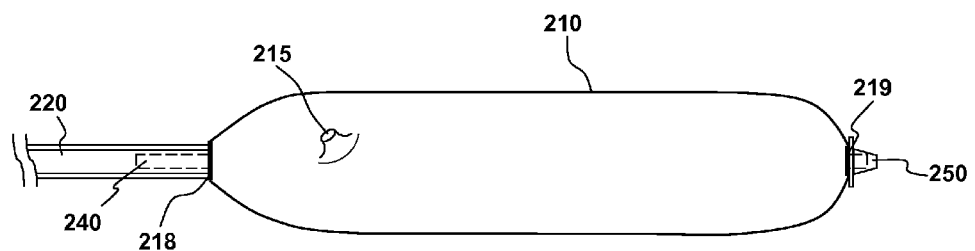
FIG. 2B shows the system of FIG. 2A as it appears when the housing is closed.

An embodiment in accordance with the present invention that incorporates the above-mentioned modification is illustrated in FIGS. 2A and 2B. The system comprises a housing 210, a catheter 220 bearing a stent 230, and a hollow stylet 240. Housing 210 includes first and second housing portions 211 and 212 and a protective well 213. Second housing portion 212 has an environmental control port 215 that permits the interior of housing 210, specifically well 213, to be subjected to a controlled environment. Housing 210 further includes a sealing member 216 and may include a latching mechanism (not shown). Housing 210 receives the distal portion of catheter 220 that bears stent 230. Stent 230 is suspended between first and second housing portions 211 and 212 in protective well 213. A proximal portion of catheter 220 extends from the proximal end of housing 210 through opening 218. Hollow stylet 240 is received within a distal portion of catheter 220. A distal portion of stylet 240 extends from the distal end of housing 210 through opening 219. A cap 250 is removably attached to the distal end of stylet 240.

As illustrated in FIG. 2A, housing 210 comprises two portions: first housing portion 211 and second housing portion 212. The two portions of housing 210 may be separated to facilitate placing a distal portion of catheter 220, which carries stent 230, within the housing. When housing 210 is closed, as shown in FIG. 2B, stent 230 is suspended between the two housing portions within protective well 213, ensuring there is little or no contact between the stent and the housing.

Protective well 213 is subjected to a controlled environment via control port 215, which is included in second housing portion 212. Ambient air may contain moisture and contaminants that could damage a coated or treated stent. Port 215 may be used to withdraw the ambient air from within protective well 213, resulting in a vacuum within the well. Alternatively, port 215 may be used to replace the ambient air within the protective well with an inert gas such as nitrogen. It will be apparent to one skilled in the art that the environmental control port may be located in either portion of housing 210.

A sealing member 216, for example a gasket, aids in maintaining a controlled environment within housing 210. When housing portions 211 and 212 are closed, sealing member 216 seals the edges of the two portions one to the other. The same or a separate sealing member encircles catheter 220 at opening 218, sealing housing 210 at the point where the proximal portion of catheter 120 extends out from the housing. The same or a separate sealing member also encircles stylet 240 at opening 219 to provide a seal at the distal end of the housing. Where one or both of the material and the structure of housing 210 permits the edges of the housing to be self-sealing, a separate sealing member may be unnecessary or may be needed only within openings 218 and 219.

Stylet 240 is inserted into a distal end of catheter 220, typically within an inner member of the catheter, before the catheter is placed into housing 210. The stylet extends to at least the proximal edge of housing 210 to preclude compression of catheter 220 by the edges of opening 218 when the catheter is closed in housing 210. Stylet 240 also serves as a sub-support for catheter 220 to prevent radial compression of the catheter lumen when a vacuum is pulled within housing 210 or when a gas is delivered into the housing.

A hollow stylet is used to provide a port through which a fluid may be injected into catheter 220 using a syringe and needle. A saline solution is commonly flushed through a catheter immediately prior to use to confirm patency of the catheter and to increase lubricity of the inner lumen of the catheter, for example to aid in passing the catheter over a guidewire. By serving as the injection port into which the needle is placed, the hollow stylet protects the catheter's tip from being damaged by the needle. Because the hollow stylet is inserted into the catheter prior to shipment, the end user need not employ a separate flushing cannula, often provided by catheter manufacturers to be inserted into the tip of a catheter, saving the end user time when preparing the catheter for use.

As shown in FIGS. 2A and 2B, a portion of hollow stylet 240 and cap 250 extend from the distal end of housing 210 through opening 219. Thus, cap 250 may be removed from stylet 240 and a needle inserted into the stylet without opening housing 210, allowing catheter 220 to be flushed with the housing in place, further protecting a coated stent from contact with the fluid used to flush the catheter.

Housing 210 may comprise one or more suitable materials that can be conventionally formed and processed. Materials such as aluminum, stainless steel, polypropylene, polyethylene, polytetrafluoroethylene (PTFE), or a nylon/polyethylene blend may be used to provide additional protection for a coated stent by minimizing exchange of chemical components between the housing and the stent should the stent inadvertently come into contact with the housing during shipment and storage.

Housing 210 may be formed using one or more methods such as blow molding or injection molding. As just one example, housing 110 may be injection molded using PTFE, and an aluminum coating may be applied to one or both of the interior and exterior surfaces of the housing. PTFE and aluminum do not react with most stent coatings, and aluminum offers the additional benefit of protecting the stent from ultraviolet rays, which can damage some coatings.

In practice, a distal portion of a catheter bearing a treatment device is enclosed within a housing. The housing holds the treatment device suspended such that there is little or no contact between the housing and the device. The catheter and housing may then be inserted into an outer package such as a hoop. The housing prevents contact between the treatment device and the wall of the hoop, both during insertion of the catheter into the hoop and during storage of the catheter. The suspended device is protected from physical damage and, when the treatment device is a stent that includes a therapeutic coating, the therapeutic coating is protected from the risk of impaired performance resulting from a therapeutic agent migrating out of the coating and into the packaging material or components of the packaging material migrating into the therapeutic coating. A hollow stylet inserted into the end of the catheter before the catheter is placed in the housing offers sub-support for an inner lumen of the catheter and also provides an injection port through which the catheter may be flushed with a fluid immediately prior to use, eliminating the need for a separate flushing cannula.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A packaged system for treating a vascular condition, comprising:
    a treatment device;
    a catheter, a distal portion of the catheter bearing the treatment device;
    a housing to receive the distal portion of the catheter bearing the treatment device and suspend the device in a protective well, the housing including a first portion rotatably attached to a second portion, the housing defining an opening through the housing into the protective well operable to receive the catheter; and a sealing member operable to encircle the catheter at the opening when the housing is closed;

wherein the protective well comprises a central portion, a distal portion and a proximal portion, the distal portion and the proximal portion having narrower cross-sections than the central portion; and wherein the protective well provides a controlled environment selected from the group consisting of a vacuum and inert gas about the treatment device when the housing is closed.

2. The system of claim 1 wherein the housing includes an environmental control port.

3. The system of claim 1 wherein the sealing member is a first sealing member and the system further comprises a second sealing member disposed around an edge of at least one of the first portion and the second portion.

4. The system of claim 1 wherein the housing includes a latching mechanism.

5. The system of claim 1 wherein the housing is fabricated using one or more materials selected from a group consisting of aluminum, stainless steel, polypropylene, polyethylene, polytetrafluoroethylene (PTFE), a nylon/polyethylene blend, and a material that minimizes exchange of chemical components between the housing and a stent during shipment and storage.

6. The system of claim 1 further comprising:
a stylet received within a distal end of the catheter.

7. The system of claim 6 wherein the stylet extends within the catheter to at least a proximal edge of the housing.

8. The system of claim 6 wherein the stylet is hollow and wherein the hollow stylet provides an injection port to allow the catheter to be flushed with a fluid prior to use.

9. The system of claim 8 further comprising:
a cap removably attached to a distal end of the hollow stylet.

10. The system of claim 1 further comprising an elongate receiving portion extending from the distal portion of the protective well.

11. A packaged system for treating a vascular condition, comprising:
a treatment device;
a catheter, a distal portion of the catheter bearing the treatment device;
a housing including a first portion and a second portion, the first portion and the second portion defining a protective well, the protective well having a central portion, a distal portion and a proximal portion, the distal portion and the proximal portion having narrower cross-sections than the central portion, the distal portion sized to contact and hold a distal tip of the catheter, the housing defining an opening through the housing into the protective well operable to receive the catheter; and
a sealing member operable to encircle the catheter at the opening when the housing is closed;
wherein the treatment device carried on the catheter is suspended between the two housing portions in the central portion of the protective well; and wherein the protective well provides a controlled environment selected from the group consisting of a vacuum and inert gas about the treatment device when the housing is closed.

12. The system of claim 11 wherein the sealing member is a first sealing member and the system further comprises a second sealing member disposed around an edge of at least one of the first portion and the second portion.

13. The system of claim 11 wherein the housing includes a latching mechanism.

14. The system of claim 11 further comprising:
a stylet received within a distal end of the catheter.

15. The system of claim 14 wherein the stylet extends within the catheter to at least a proximal edge of the housing.

16. The system of claim 14 wherein the stylet is hollow and wherein the hollow stylet provides an injection port to allow the catheter to be flushed with a fluid prior to use.

17. The system of claim 16 further comprising:
a cap removably attached to a distal end of the hollow stylet.

18. The system of claim 11 further comprising an environmental control port disposed within the housing.

19. A packaged system for treating a vascular condition, comprising:
a treatment device;
a catheter, a distal portion of the catheter bearing the treatment device;
a housing to receive the treatment device and suspend the device in a central portion of a protective well, the protective well having a distal portion for contacting and holding a distal tip of the catheter, the protective well providing a controlled environment selected from the group consisting of a vacuum and inert gas about the treatment device when the housing is closed, the housing defining an opening through the housing into the protective well operable to receive the catheter;
a sealing member operable to encircle the catheter at the opening when the housing is closed; and
a hollow stylet received within a distal end of the catheter, wherein the hollow stylet provides an injection port to allow the catheter to be flushed with a fluid prior to use.

20. The system of claim 19 further comprising:
a cap removably attached to a distal end of the hollow stylet.

21. The system of claim 19 wherein the sealing member is a first sealing member and the system further comprises a second sealing member disposed around an edge of at least one of the first portion and the second portion.

22. The system of claim 19 wherein the housing includes an environmental control port.

23. The system of claim 19 wherein the hollow stylet extends within the catheter to at least a proximal edge of the housing.

24. The system of claim 19 wherein the housing is fabricated using one or more materials selected from a group consisting of aluminum, stainless steel, polypropylene, polyethylene, a nylon/polyethylene blend, polytetrafluoroethylene (PTFE), and a material that minimizes exchange of chemical components between a stent and the housing during shipment and storage.

* * * * *